US007256219B2

(12) United States Patent
Cai et al.

(10) Patent No.: US 7,256,219 B2
(45) Date of Patent: Aug. 14, 2007

(54) MULTIFLUORO-SUBSTITUTED CHALCONES AND ANALOGS AS ACTIVATORS OF CASPASES AND INDUCERS OF APOPTOSIS AND THE USE THEREOF

(75) Inventors: Sui Xiong Cai, San Diego, CA (US); P. Sanjeeva Reddy, San Diego, CA (US); John A. Drewe, Carlsbad, CA (US); Bao Ngoc Nguyen, San Diego, CA (US); Shailaja Kasibhatla, San Diego, CA (US)

(73) Assignee: Cytovia, Inc., San Diego, CA (US)

( * ) Notice: Subject to any disclaimer, the term of this patent is extended or adjusted under 35 U.S.C. 154(b) by 559 days.

(21) Appl. No.: 10/471,720

(22) PCT Filed: Mar. 14, 2002

(86) PCT No.: PCT/US02/07569

§ 371 (c)(1),
(2), (4) Date: Oct. 16, 2003

(87) PCT Pub. No.: WO02/072544

PCT Pub. Date: Sep. 19, 2002

(65) Prior Publication Data

US 2004/0171637 A1  Sep. 2, 2004

Related U.S. Application Data

(60) Provisional application No. 60/275,473, filed on Mar. 14, 2001.

(51) Int. Cl.
| | |
|---|---|
| A61K 31/12 | (2006.01) |
| C07C 49/00 | (2006.01) |
| C07D 333/00 | (2006.01) |
| C07D 307/02 | (2006.01) |
| C07D 221/02 | (2006.01) |
| C07D 209/04 | (2006.01) |
| C07D 207/18 | (2006.01) |

(52) U.S. Cl. ............... 514/681; 514/685; 568/327; 568/334; 549/49; 549/379; 549/505; 546/112; 548/469; 548/565

(58) Field of Classification Search ............ 514/740, 514/765, 681, 685; 568/327, 334; 549/49, 549/379, 505; 546/112; 548/469, 565
See application file for complete search history.

(56) References Cited

U.S. PATENT DOCUMENTS

| | | | |
|---|---|---|---|
| 5,144,029 A | 9/1992 | Ward et al. | |
| 5,739,163 A | 4/1998 | Cain et al. | |

FOREIGN PATENT DOCUMENTS

| | | | |
|---|---|---|---|
| WO | WO99/18856 | 4/1999 | |

OTHER PUBLICATIONS

Howell, A. Overview of the impact of conventional systemic therapies on breast cancer (2005) Endocrine-Related Cancer 12: S9-S16.*
Heenen, M., et al., "Methotrexate induces apoptotic cell death in human keratinocytes," *Arch. Dermatol. Res.* 290:240-245, Springer-Verlag (1998).
Infante, A.J., et al., "The clinical spectrum in a large kindred with autoimmune lymphoproliferative syndrome caused by a Fas mutation that impairs lymphocyte apoptosis," *J. Pediatr.* 133:629-633, Mosby, Inc. (1998).
Leu, Y.-L., et al., "Design and Synthesis of Water-Soluble Glucuronide Derivatives of Camptothecin for Cancer Prodrug Monotherapy and Antibody-Directed Enzyme Prodrug Therapy (ADEPT)," *J. Med. Chem.* 42:3623-3628, American Chemical Society (1999).
López-Hoyos, M., et al., "Regulation of B Cell apoptosis by Bcl-2 and Bcl-$X_L$ and its role in the development of autoimmune diseases (Review)," *Int. J. Mol. Med.* 1:475-483, D.A. Spandidos (1998).
Los, M., et al., "Cross-Resistance of CD95- and Drug-Induced Apoptosis as a Consequence of Deficient Activation of Caspases (ICE/Ced-3 Proteases)," *Blood* 90:3118-3129, W. B. Saunders (1997).
Ohsako, S., and Elkon, K.B., "Apoptosis in the effector phase of autoimmune diabetes, multiple sclerosis and thyroiditis," *Cell Death Differ.* 6:13-21, Stockton Press (1999).
O'Reilly, L.A., and Strasser, A., "Apoptosis and aútoimmune disease," *Inflamm. Res.* 48:5-21, Birkhäuser Verlag (1999).
Ozawa, M., et al., "312-nanometer Ultraviolet B Light (Narrow-Band UVB) Induces Apoptosis of T Cells within Psoriatic Lesions," *J. Exp. Med.* 189:711-718, The Rockefeller University Press (1999).

(Continued)

*Primary Examiner*—Sreeni Padmanabhan
*Assistant Examiner*—Renee Claytor
(74) *Attorney, Agent, or Firm*—Sterne, Kessler, Goldstein & Fox P.L.L.C.

(57) ABSTRACT

The present invention is directed to multifluoro-substituted Chalcones and analogs thereof, represented by the general Formula I:

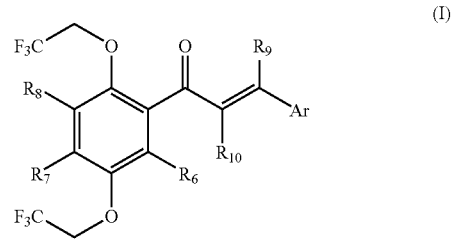

(I)

wherein Ar and $R_6$-$R_{10}$ are defined herein. The present invention also relates to the discovery that compounds having Formula I are activators of caspases and inducers of apoptosis. Therefore, the activators of caspases and inducers of apoptosis of this invention may be used to induce cell death in a variety of clinical conditions in which uncontrolled growth and spread of abnormal cells occurs.

8 Claims, 1 Drawing Sheet

OTHER PUBLICATIONS

Savill, J., "Apoptosis in resolution of inflammation," *J. Leukoc. Biol.* 61:375-380, The Society for Leukocyte Biology (1997).

Schmitt, E., et al., "The Bcl-xL and Bax-α control points: modulation of apoptosis induced by cancer chemotherapy and relation to TPCK-sensitive protease and caspase activation," *Biochem. Cell Biol.* 75:301-314, National Research Council of Canada (1997).

Tai, D-I., et al., "Activation of Nuclear Factor κB in Hepatits C Virus Infection: Implications for Pathogenesis and Hepatocarcinogenesis," *Hepatology* 31:656-664, W.B. Saunders Co. (Mar. 2000).

Vaishnaw, A.K., et al., "The molecular basis for apoptotic defects in patients with CD95 (Fas/Apo-1) mutations," *J. Clin. Invest.* 103:355-363, The American Society for Clinical Investigation (1999).

Wakisaka, S., et al., "Modulation by proinflammatory cytokines of Fas/Fas ligand-mediated apoptotic cell death of synovial cells in patients with rheumatoid arthritis (RA)," *Clin. Exp. Immunol.* 114:119-128, Blackwell Science (1998).

Zhou, T., et al., "Bisindolylmaleimide VIII facilitates Fas-mediated apoptosis and inhibits T cell-mediated autoimmune diseases," *Nat. Med.* 5:42-48, Nature Publishing Co. (1999).

International Search Report for International Application No. PCT/US02/07569, 3 pages, ISA.US, Commissioner of Patents and Trademarks, Washington, D.C. (mailed Sep. 25, 2002).

Batteux, F., et al., "Gene Therapy of Experimental Autoimmune Thyroiditis by In Vivo Administration of Plasmid DNA Coding for Fas Ligand," *J. Immunol.* 162:603-608, American Association of Immunologists (1999).

Boirivant, M., et al., "Lamina Propria T Cells in Crohn's Disease and Other Gastrointestinal Inflammation Show Defective CD2 Pathway-Induced Apoptosis," *Gastroenterology* 116:557-565, W.B. Saunders (1999).

Chinnaiyan, A.M., et al., "The inhibition of pro-apoptotic ICE-like proteases enhances HIV replication," *Nat. Med.* 3:333-337, Nature Pub. Co. (1997).

Coven, T.R., et al., "PUVA-induced lymphocyte apoptosis: Mechanism of action in psoriasis," *Photodermatol. Photoimmunol. Photomed.* 15:22-27, Blackwell Munksgaard (1999).

Friesen, C., et al., "Involvement of the CD95 (APO-1/Fas) receptor/ligand system in drug-induced apoptosis in leukemia cells," *Nat. Med.* 2:574-577, Nature Pub. Co. (1996).

Greenwald, R.B., et al., "Drug Delivery Systems Employing 1,4- or 1,6-Elimination: Poly(ethylene glycol) Prodrugs of Amine-Containing Compounds," *J. Med. Chem.* 42:3657-3667, American Chemical Society (1999).

Chabner, B.A., et al., "Antineoplastic Agents" in *Goodman and Gilman's The Pharmacological Basis of Therapeutics, Ninth Edition*, Chapter 51, Hardman, J.G., et al., eds., McGraw-Hill, New York, NY, pp. 1233-1287 (1996).

Los, M., et al., "Cross-Resistance of CD95- and Drug-Induced Apoptosis as a Consequence of Deficient Activation of Caspases (ICE/Ced-3 Proteases)," *Blood* 90:3118-3129, American .Society of Hematology (1997).

Ohsako, S., and Elkon, K.B., "Apoptosis in the effector phase of autoimmune diabetes, multiple sclerosis and thyroiditis," *Cell Death Differ.* 6:13-21, Nature Pub. Co. (1999).

O'Reilly, L.A., and Strasser, A., "Apoptosis and autoimmune disease," *Inflamm. Res.* 48:5-21, Birkhäuser (1999).

Savill, J., "Apoptosis in resolution of inflammation," *J. Leukoc. Biol.* 61:375-380, Federation of American Societies for Experimental Biology (1997).

Tai, D-I., et al., "Activation of Nuclear Factor κB in Hepatits C Virus Infection: Implications for Pathogenesis and Hepatocarcinogenesis," *Hepatology* 31:656-664, W.B. Saunders (2000).

Wakisaka, S., et al., "Modulation by proinflammatory cytokines of Fas/Fas ligand-mediated apoptotic cell death of synovial cells in patients with rheumatoid arthritis (RA)," *Clin. Exp. Immunol.* 114:119-128, Blackwell Scientific Publications (1998).

Zhou, T., et al., "Bisindolylmaleimide VIII facilitates Fas-mediated apoptosis and inhibits T Cell-mediated autoimmune diseases," *Nat. Med.* 5:42-48, Nature Pub. Co. (1999).

International Search Report for PCT Application No. PCT/US02/07569, mailed Sep. 25, 2002, 2 pages, United States International Searching Authority, Washington, DC.

* cited by examiner

MULTIFLUORO-SUBSTITUTED CHALCONES AND ANALOGS AS ACTIVATORS OF CASPASES AND INDUCERS OF APOPTOSIS AND THE USE THEREOF

BACKGROUND OF THE INVENTION

1. Field of the Invention

This invention is in the field of medicinal chemistry. In particular, the invention relates to multifluoro-substituted chalcones and analogs, and the discovery that these compounds are activators of caspases and inducers of apoptosis. The invention also relates to the use of these compounds as therapeutically effective anti-cancer agents.

2. Related Art

Organisms eliminate unwanted cells by a process variously known as regulated cell death, programmed cell death or apoptosis. Such cell death occurs as a normal aspect of animal development as well as in tissue homeostasis and aging (Glucksmann, A., *Biol. Rev. Cambridge Philos. Soc.* 26:59-86 (1951); Glucksmann, A., *Archives de Biologie* 76:419-437 (1965); Ellis, et al., *Dev.* 112:591-603 (1991); Vaux, et al., *Cell* 76:777-779 (1994)). Apoptosis regulates cell number, facilitates morphogenesis, removes harmful or otherwise abnormal cells and eliminates cells that have already performed their function. Additionally, apoptosis occurs in response to various physiological stresses, such as hypoxia or ischemia (PCT published application WO96/20721).

There are a number of morphological changes shared by cells experiencing regulated cell death, including plasma and nuclear membrane blebbing, cell shrinkage (condensation of nucleoplasm and cytoplasm), organelle relocalization and compaction, chromatin condensation and production of apoptotic bodies (membrane enclosed particles containing intracellular material) (Orrenius, S., *J. Internal Medicine* 237:529-536 (1995)).

Apoptosis is achieved through an endogenous mechanism of cellular suicide (Wyllie, A. H., in *Cell Death in Biology and Pathology*, Bowen and Lockshin, eds., Chapman and Hall (1981), pp. 9-34). A cell activates its internally encoded suicide program as a result of either internal or external signals. The suicide program is executed through the activation of a carefully regulated genetic program (Wyllie, et al., *Int. Rev. Cyt.* 68:251 (1980); Ellis, et al., *Ann. Rev. Cell Bio.* 7:663 (1991)). Apoptotic cells and bodies are usually recognized and cleared by neighboring cells or macrophages before lysis. Because of this clearance mechanism, inflammation is not induced despite the clearance of great numbers of cells (Orrenius, S., *J. Internal Medicine* 237:529-536 (1995)).

It has been found that a group of proteases are a key element in apoptosis (see, e.g., Thornberry, *Chemistry and Biology* 5:R97-R103 (1998); Thornberry, *British Med. Bull.* 53:478-490 (1996)). Genetic studies in the nematode *Caenorhabditis elegans* revealed that apoptotic cell death involves at least 14 genes, two of which are the pro-apoptotic (death-promoting) ced (for cell death abnormal) genes, ced-3 and ced-4. CED-3 is homologous to interleukin 1 beta-converting enzyme, a cysteine protease, which is now called caspase-1. When these data were ultimately applied to mammals, and upon further extensive investigation, it was found that the mammalian apoptosis system appears to involve a cascade of caspases, or a system that behaves like a cascade of caspases. At present, the caspase family of cysteine proteases comprises 14 different members, and more may be discovered in the future. All known caspases are synthesized as zymogens that require cleavage at an aspartyl residue prior to forming the active enzyme. Thus, caspases are capable of activating other caspases, in the manner of an amplifying cascade.

Apoptosis and caspases are thought to be crucial in the development of cancer (*Apoptosis and Cancer Chemotherapy*, Hickman and Dive, eds., Humana Press (1999)). There is mounting evidence that cancer cells, while containing caspases, lack parts of the molecular machinery that activates the caspase cascade. This makes the cancer cells lose their capacity to undergo cellular suicide and the cells become cancerous. In the case of the apoptosis process, control points are known to exist that represent points for intervention leading to activation. These control points include the CED-9-BCL-like and CED-3-ICE-like gene family products, which are intrinsic proteins regulating the decision of a cell to survive or die and executing part of the cell death process itself, respectively (see, Schmitt, et al., *Biochem. Cell. Biol.* 75:301-314 (1997)). BCL-like proteins include BCL-xL and BAX-alpha, which appear to function upstream of caspase activation. BCL-xL appears to prevent activation of the apoptotic protease cascade, whereas BAX-alpha accelerates activation of the apoptotic protease cascade.

It has been shown that chemotherapeutic (anti-cancer) drugs can trigger cancer cells to undergo suicide by activating the dormant caspase cascade. This may be a crucial aspect of the mode of action of most, if not all, known anticancer drugs (Los, et al., *Blood* 90:3118-3129 (1997); Friesen, et al., *Nat. Med.* 2:574 (1996)). The mechanism of action of current antineoplastic drugs frequently involves an attack at specific phases of the cell cycle. In brief, the cell cycle refers to the stages through which cells normally progress during their lifetimes. Normally, cells exist in a resting phase termed $G_o$. During multiplication, cells progress to a stage in which DNA synthesis occurs, termed S. Later, cell division, or mitosis occurs, in a phase called M. Antineoplastic drugs such as cytosine arabinoside, hydroxyurea, 6-mercaptopurine, and methotrexate are S phase specific, whereas antineoplastic drugs such as vincristine, vinblastine, and paclitaxel are M phase specific. Many slow growing tumors, for example colon cancers, exist primarily in the $G_o$ phase, whereas rapidly proliferating normal tissues, for example bone marrow, exist primarily in the S or M phase. Thus, a drug like 6-mercaptopurine can cause bone marrow toxicity while remaining ineffective for a slow growing tumor. Further aspects of the chemotherapy of neoplastic diseases are known to those skilled in the art (See, e.g., Hardman, et al., eds., *Goodman and Gilman's The Pharmacological Basis of Therapeutics*. Ninth Edition, McGraw-Hill, New York (1996), pp. 1225-1287). Thus, it is clear that the possibility exists for the activation of the caspase cascade, although the exact mechanisms for doing so are not clear at this point. It is equally clear that insufficient activity of the caspase cascade and consequent apoptotic events are implicated in various types of cancer. The development of caspase cascade activators and inducers of apoptosis is a highly desirable goal in the development of therapeutically effective antineoplastic agents. Caspase cascade activators and inducers of apoptosis could also be a desirable therapy in the elimination of pathogens such as HIV, Hepatitis C and other viral pathogens. The long lasting quiescence followed by a disease progression may be explained by anti-apoptotic mechanism of these pathogens leading to persistent cellular reservoirs of the virions. It has been reported that HIV-1 infected T leukemia cells or peripheral blood mononuclear cells (PBMCs) underwent enhanced viral replication in the presence of caspase inhibitor Z-VAD-fmk. Furthermore, Z-VAD-fmk also stimulated endogenous virus production in activated PBMCs derived from HIV-1-infected asymptomatic individuals (Chinnaiyan, A. et. al. *Nature Medicine*. 3:333. 1997). Therefore apoptosis may serve as a beneficial host mechanism to limit HIV spread and new therapeutics using caspase/apoptosis activators could be useful to clear viral reservoirs from the infected individuals. Similarly, HCV infection also triggers anti apoptotic mechanisms to evade host's immune surveillance leading to viral persistence and hepatocarcinogenesis (Tai DI et. al. Hepatology 3: 656-64, 2000). Therefore apoptosis inducers could be useful as therapeutics for HCV and other infectious disease. Moreover, since autoimmune disease and certain degenerative diseases also involve the proliferation of abnormal cells, therapeutic treatment for these diseases could also involve the enhancement of the apoptotic process through the administration of appropriate caspase cascade activators and inducers of apoptosis.

SUMMARY OF THE INVENTION

The present invention is related to the discovery that multifluoro-substituted chalcones and analogs, as represented in Formula I, are activators of the caspase cascade and inducers of apoptosis. Thus, an aspect of the present invention is directed to the use of compounds of Formula I as inducers of apoptosis.

The compounds of the present invention are represented by Formula I:

(I)

or pharmaceutically acceptable salts or prodrugs thereof, wherein:

Ar is optionally substituted aryl or optionally substituted heteroaryl;

$R_6$-$R_8$ are independently hydrogen, halo, haloalkyl, aryl, fused aryl, carbocyclic, a heterocyclic group, a heteroaryl group, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, amino, cyano, acylamido, hydroxy, thiol, acyloxy, azido, alkoxy, aryloxy, arylalkoxy, haloalkoxy, carboxy, carbonylamido or alkylthiol;

$R_9$ and $R_{10}$ are independently hydrogen, alkyl, or cycloalkyl.

A second aspect of the present invention is to provide a method for treating, preventing or ameliorating neoplasia and cancer by administering a compound of Formula I to a mammal in need of such treatment.

A third aspect of the present invention is to provide a method for treating, preventing or ameliorating an infectious viral disease, e.g. HIV infection and hepatitis C infection, by administering a compound of Formula I to a mammal in need of such treatment.

Many of the compounds within the scope of the present invention are novel compounds. Therefore, a fourth aspect of the present invention is to provide novel compounds of Formula I, and to also provide for the use of these novel compounds for treating, preventing or ameliorating neoplasia and cancer.

A fifth aspect of the present invention is to provide a pharmaceutical composition useful for treating disorders responsive to the induction of apoptosis, containing an effective amount of a compound of Formula I in admixture with one or more pharmaceutically acceptable carriers or diluents.

A sixth aspect of the present invention is directed to methods for the preparation of novel compounds of Formula I.

BRIEF DESCRIPTION OF THE DRAWINGS/FIGURES

FIGS. 1A-B are graphs showing drug induced cell cycle arrest and apoptosis in T47D cells. FIG. 1A: control cells showing most of the cells in G1(M2). FIG. 1B: cells treated with 10 µM of 1-[2,5-bis(2,2,2-trifluoroethoxy)phenyl]-3-[4-(trifluoromethyl)phenyl]-2-propen-1-one for 24 h showing an increase of sub-diploid DNA content of cells (M1).

DETAILED DESCRIPTION OF THE INVENTION

The present invention arises out of the discovery that multifluoro-substituted chalcones and analogs, as represented in Formula I, are potent and highly efficacious activators of the caspase cascade and inducers of apoptosis. Therefore compounds of Formula I are useful for treating disorders responsive to induction of apoptosis.

Specifically, compounds useful in this aspect of the present invention are represented by Formula I:

(I)

or pharmaceutically acceptable salts or prodrugs thereof, wherein:

Ar is optionally substituted aryl or optionally substituted heteroaryl;

$R_6$-$R_8$ are independently hydrogen, halo, haloalkyl, aryl, fused aryl, carbocyclic, a heterocyclic group, a heteroaryl group, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, amino, cyano, acylamido, hydroxy, thiol, acyloxy, azido, alkoxy, aryloxy, arylalkoxy, haloalkoxy, carboxy, carbonylamido or alkylthiol;

$R_9$ and $R_{10}$ are independently hydrogen, alkyl or cycloalkyl.

Preferred compounds of Formula I include compounds wherein Ar is optionally substituted phenyl, naphthyl, pyridyl, quinolyl, isoquinolyl, thienyl, furyl, or pyrrolyl.

Preferred compounds of Formula I also include compounds wherein $R_9$ and $R_{10}$ are hydrogen.

Especially preferred compounds of Formula I are multi-fluoro-substituted chalcones and analogs represented by Formula II:

(II)

or pharmaceutically acceptable salts or prodrugs thereof, wherein:

$R_1$-$R_8$ are independently hydrogen, halo, haloalkyl, aryl, fused aryl, carbocyclic, a heterocyclic group, a heteroaryl group, alkyl, alkenyl, alkynyl, arylalkyl. arylalkenyl. arylalkynyl, heteroarylalkyl, heteroarylalkenyl, heteroarylalkynyl, carbocycloalkyl, heterocycloalkyl, hydroxyalkyl, nitro, amino, cyano, acylamido, hydroxy, thiol, acyloxy, azido, alkoxy, aryloxy, arylalkoxy, haloalkoxy, carboxy, carbonylamido or alkylthiol.

Exemplary preferred compounds that may be employed in the method of the invention include, without limitation:

1-[2,5-bis(2,2,2-trifluoroethoxy)phenyl]-3-[4-(trifluoromethyl)phenyl]-2-propen-1-one;

1-[2,5-bis(2,2,2-trifluoroethoxy)phenyl]-3-(4-methoxyphenyl)-2-propen-1-one;

1-[2,5-bis(2,2,2-trifluoroethoxy)phenyl]-3-(2-methoxyphenyl)-2-propen-1-one;

1-[2,5-bis(2,2,2-trifluoroethoxy)phenyl]-3-phenyl-2-propen-1-one;

1-[2,5-bis(2,2,2-trifluoroethoxy)phenyl]-3-[3-(trifluoromethyl)phenyl]-2-propen-1-one;

1-[2,5-bis(2,2,2-trifluoroethoxy)phenyl]-3-(3-methoxyphenyl)-2-propen-1-one;

1-[2,5-bis(2,2,2-trifluoroethoxy)phenyl]-3-(2-chlorophenyl)-2-propen-1-one;

1-[2,5-bis(2,2,2-trifluoroethoxy)phenyl]-3-(2-methylphenyl)-2-propen-1-one;

1-[2,5-bis(2,2,2-trifluoroethoxy)phenyl]-3-(4-nitrophenyl)-2-propen-1-one;

1-[2,5-bis(2,2,2-trifluoroethoxy)phenyl]-3-(2-pyridyl)-2-propen-1-one;

1-[2,5-bis(2,2,2-trifluoroethoxy)phenyl]-3-(3-pyridyl)-2-propen-1-one;

1-[2,5-bis(2,2,2-trifluoroethoxy)phenyl]-3-(2,3-difluoro-4-trifluoromethylphenyl)-2-propen-1-one; and 1-[2,5-bis(2,2,2-trifluoroethoxy)phenyl]-3-(3-fluoro-4-trifluoromethyl-phenyl)-2-propen-1-one.

The present invention is also directed to novel compounds within the scope of Formulae I-II. Exemplary preferred compounds that may be employed in this invention include, without limitation:

1-[2,5-bis(2,2,2-trifluoroethoxy)phenyl]-3-(4-methylphenyl)-2-propen-1-one;

1-[2,5-bis(2,2,2-trifluoroethoxy)phenyl]-3-(4-methoxyphenyl)-2-propen-1-one;

1-[2,5-bis(2,2,2-trifluoroethoxy)phenyl]-3-(2-methoxyphenyl)-2-propen-1-one;

1-[2,5-bis(2,2,2-trifluoroethoxy)phenyl]-3-phenyl-2-propen-1-one;

1-[2,5-bis(2,2,2-trifluoroethoxy)phenyl]-3-(4-chlorophenyl)-2-propen-1-one;

1-[2,5-bis(2,2,2-trifluoroethoxy)phenyl]-3-[2-(trifluoromethyl)phenyl]-2-propen-1-one;

1-[2,5-bis(2,2,2-trifluoroethoxy)phenyl]-3-(3,4-dimethoxyphenyl)-2-propen-1-one;

1-[2,5-bis(2,2,2-trifluoroethoxy)phenyl]-3-(3,4,5-trimethoxyphenyl)-2-propen-1-one;

1-[2,5-bis(2,2,2-trifluoroethoxy)phenyl]-3-[3-(trifluoromethyl)phenyl]-2-propen-1-one;

1-[2,5-bis(2,2,2-trifluoroethoxy)phenyl]-3-(3-methoxyphenyl)-2-propen-1-one;

1-[2,5-bis(2,2,2-trifluoroethoxy)phenyl]-3-(3-methylphenyl)-2-propen-1-one;

1-[2,5-bis(2,2,2-trifluoroethoxy)phenyl]-3-(2-chlorophenyl)-2-propen-1-one;

1-[2,5-bis(2,2,2-trifluoroethoxy)phenyl]-3-(2-methylphenyl)-2-propen-1-one;

1-[2,5-bis(2,2,2-trifluoroethoxy)phenyl]-3-(4-nitrophenyl)-2-propen-1-one;

1-[2,5-bis(2,2,2-trifluoroethoxy)phenyl]-3-(2-pyridyl)-2-propen-1-one;

1-[2,5-bis(2,2,2-trifluoroethoxy)phenyl]-3-(3-pyridyl)-2-propen-1-one;

1-[2,5-bis(2,2,2-trifluoroethoxy)phenyl]-3-(3-nitrophenyl)-2-propen-1-one;

1-[2,5-bis(2,2,2-trifluoroethoxy)phenyl]-3-[2,4-di(trifluoromethyl)-phenyl]-2-propen-1-one;

1-[2,5-bis(2,2,2-trifluoroethoxy)phenyl]-3-(4-ethoxyphenyl)-2-propen-1-one;

1-[2,5-bis(2,2,2-trifluoroethoxy)phenyl]-3-(2,3-difluoro-4-trifluoro-methylphenyl)-2-propen-1-one; and 1-[2,5-bis(2,2,2-trifluoroethoxy)phenyl]-3-(3-fluoro-4-trifluoro-methylphenyl)-2-propen-1-one.

Useful alkyl groups include straight-chained and branched $C_{1-10}$ alkyl groups, more preferably $C_1$-$C_6$ alkyl groups. Typical $C_{1-10}$ alkyl groups include methyl, ethyl, propyl, isopropyl, butyl, sec-butyl, tert-butyl, 3-pentyl, hexyl and octyl groups, which may be optionally substituted.

Useful alkoxy groups include oxygen substituted by one of the $C_{1-10}$ alkyl groups mentioned above, which may be optionally substituted.

Useful alkylthio groups include sulphur substituted by one of the $C_{1-10}$ alkyl groups mentioned above, which may be optionally substituted. Also included are the sulfoxides and sulfones of such alkylthio groups.

Useful alkenyl groups include straight-chained and branched $C_{2-10}$ alkenyl groups, more preferably $C_{2-6}$ alkenyl groups. Typical $C_{2-10}$ alkenyl groups include ethenyl, propenyl, isopropenyl, butenyl, 3-pentenyl, hexenyl and octenyl groups, which may be optionally substituted.

Useful alkynyl groups include straight-chained and branched $C_{2-10}$ alkynyl groups, more preferably $C_{2-6}$ alkynyl groups. Typical $C_{2-10}$ alkynyl groups include ethynyl, propynyl, butynyl, 3-pentynyl, hexynyl and octynyl groups, which may be optionally substituted.

Useful amino groups include —$NH_2$, —$NHR_{15}$ and —$NR_{15}R_{16}$, wherein $R_{15}$ and $R_{16}$ are $C_{1-10}$ alkyl or cycloalkyl groups, or $R_{15}$ and $R_{16}$ are combined with the N to form a ring structure, such as a piperidine, or $R_{15}$ and $R_{16}$ are combined with the N and other group to form a ring, such as a piperazine. The alkyl group may be optionally substituted.

Optional substituents on the alkyl, alkenyl and alkynyl groups include one or more halo, hydroxy, carboxyl, amino, nitro, cyano, $C_1$-$C_6$ acylamino, $C_1$-$C_6$ acyloxy, $C_1$-$C_6$ alkoxy, aryloxy, alkylthio, $C_6$-$C_{10}$ aryl, $C_4$-$C_7$ cycloalkyl, $C_2$-$C_6$ alkenyl, $C_2$-$C_6$ alkynyl, $C_6$-$C_{10}$ aryl($C_2$-$C_6$)alkenyl, $C_6$-$C_{10}$ aryl($C_2$-$C_6$)alkynyl, saturated and unsaturated heterocyclic or heteroaryl.

Optional substituents on the aryl, aralkyl and heteroaryl groups include one or more halo, $C_1$-$C_6$ haloalkyl, $C_6$-$C_{10}$ aryl, $C_4$-$C_7$ cycloalkyl, $C_1$-$C_6$ alkyl, $C_2$-$C_6$ alkenyl, $C_2$-$C_6$ alkynyl, $C_6$-$C_{10}$ aryl($C_1$-$C_6$)alkyl, $C_6$-$C_{10}$ aryl($C_2$-$C_6$)alkenyl, $C_6$-$C_{10}$ aryl($C_2$-$C_6$)alkynyl, $C_1$-$C_6$ hydroxyalkyl, nitro, amino, ureido, cyano, $C_1$-$C_6$ acylamino, hydroxy, thiol, $C_1$-$C_6$ acyloxy, azido, $C_1$-$C_6$ alkoxy or carboxy.

The term "aryl" as employed herein by itself or as part of another group refers to monocyclic, bicyclic or tricyclic aromatic groups containing from 6 to 14 carbons in the ring portion.

Useful aryl groups include $C_{6-14}$ aryl, preferably $C_{6-10}$ aryl. Typical $C_{6-14}$ aryl groups include phenyl, naphthyl, phenanthrenyl, anthracenyl, indenyl, azulenyl, biphenyl, biphenylenyl and fluorenyl groups.

Useful cycloalkyl groups are $C_{3-8}$ cycloalkyl. Typical cycloalkyl groups include cyclopropyl, cyclobutyl, cyclopentyl, cyclohexyl and cycloheptyl.

Useful saturated or partially saturated carbocyclic groups are cycloalkyl groups as described above, as well as cycloalkenyl groups, such as cyclopentenyl, cycloheptenyl and cyclooctenyl.

Useful halo or halogen groups include fluorine, chlorine, bromine and iodine.

Useful arylalkyl groups include any of the above-mentioned $C_{1-10}$ alkyl groups substituted by any of the above-mentioned $C_{6-14}$ aryl groups. Preferably the arylakyl group is benzyl, phenethyl or naphthylmethyl.

Useful haloalkyl groups include $C_{1-10}$ alkyl groups substituted by one or more fluorine, chlorine, bromine or iodine atoms, e.g., fluoromethyl, difluoromethyl, trifluoromethyl, pentafluoroethyl, 1,1-difluoroethyl, chloromethyl, chlorofluoromethyl and trichloromethyl groups.

Useful acylamino (acylamido) groups are any $C_{1-6}$ acyl (alkanoyl) attached to an amino nitrogen, e.g., acetamido, chloroacetamido, propionamido, butanoylamido, pentanoylamido and hexanoylamido, as well as aryl-substituted $C_1$-$C_6$ acylamino groups, e.g., benzoylamido, and pentafluorobenzoylamido.

Useful acyloxy groups are any $C_{1-6}$ acyl (alkanoyl) attached to an oxy (—O—) group, e.g., formyloxy, acetoxy, propionoyloxy, butanoyloxy, pentanoyloxy and hexanoyloxy.

The term heterocycle is used herein to mean a saturated or partially saturated 3-7 membered monocyclic, or 7-10 membered bicyclic ring system, which consists of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on carbon or on a nitrogen atom if the resulting compound is stable.

Useful saturated or partially saturated heterocyclic groups include tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl pyrazolinyl, tetronoyl and tetramoyl groups.

The term "heteroaryl" as employed herein refers to groups having 5 to 14 ring atoms; 6, 10 or 14 π electrons shared in a cyclic array; and containing carbon atoms and 1, 2 or 3 oxygen, nitrogen or sulfur heteroactoms.

Useful heteroaryl groups include thienyl, benzo[b]thienyl, naphtho[2,3-b]thienyl, thianthrenyl, furyl, pyranyl, isobenzofuranyl, chromenyl, xanthenyl, phenoxanthiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinoxalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]pyrimidin-4-one, 1,2-benzoisoxazol-3-yl, benzimidazolyl, 2-oxindolyl and 2-oxobenzimidazolyl. Where the heteroaryl group contains a nitrogen atom in a ring, such nitrogen atom may be in the form of an N-oxide, e.g., a pyridyl N-oxide, pyrazinyl N-oxide and pyrimidinyl N-oxide.

Some of the compounds of the present invention may exist as stereoisomers including optical isomers. The invention includes all stereoisomers and both the racemic mixtures of such stereoisomers as well as the individual enantiomers that may be separated according to methods that are well known to those of ordinary skill in the art.

Examples of pharmaceutically acceptable addition salts include inorganic and organic acid addition salts such as hydrochloride, hydrobromide, phosphate, sulphate, citrate, lactate, tartrate, maleate, fumarate, mandelate and oxalate; and inorganic and organic base addition salts with bases such as sodium hydroxy, Tris(hydroxymethyl)aminomethane (TRIS, tromethane) and N-methyl-glucamine.

Examples of prodrugs of the compounds of the invention include the simple esters of carboxylic acid containing compounds (e.g., those obtained by condensation with a $C_{1-4}$ alcohol according to methods known in the art); esters of hydroxy containing compounds (e.g., those obtained by condensation with a $C_{1-4}$ carboxylic acid, $C_{3-6}$ dioic acid or anhydride thereof such as succinic and fumaric anhydrides according to methods known in the art), imines of amino containing compounds (e.g., those obtained by condensation with a $C_{1-4}$ aldehyde or ketone according to methods known in the art); carbamate of amino containing compounds such as those described by Leu, et. al., (*J. Med. Chem*. 42:3623-3628 (1999)) and Greenwald, et. al., (*J. Med. Chem*. 42:3657-3667 (1999)); and acetals and ketals of alcohol containing compounds (e.g., those obtained by condensation with chloromethyl methyl ether or chloromethyl ethyl ether according to methods known in the art).

The compounds of this invention may be prepared using methods known to those skilled in the art, or the novel methods of this invention. Specifically, the compounds of this invention with Formulae I-II may be prepared as illustrated by the exemplary reaction in Scheme 1. Reaction of 2,5-bis(2,2,2-trifluoroethoxy)acetophenone with the substituted benzaldehyde in the presence of a base such as NaOH produced the product 1-[2,5-bis(2,2,2-trifluoroethoxy)phenyl]-3-[4-(trifluoromethyl)phenyl]-2-propen-1-one.

Scheme 1

An important aspect of the present invention is the discovery that compounds having Formula I-II are activators of caspases and inducers of apoptosis. Therefore, these compounds are useful in a variety of clinical conditions in which there is uncontrolled cell growth and spread of abnormal cells, such as in the case of cancer.

Another important aspect of the present invention is the discovery that compounds having Formula I-II are potent and highly efficacious activators of caspases and inducers of apoptosis in drug resistant cancer cells, such as breast and prostate cancer cells, which enables these compounds to kill these drug resistant cancer cells. In comparison, most standard anti-cancer drugs are not effective in killing drug resistant cancer cells under the same conditions. Therefore, compounds of this invention are useful for the treatment of drug resistant cancer in animals.

The present invention includes a therapeutic method useful to modulate in vivo apoptosis or in vivo neoplastic disease, comprising administering to a subject in need of such treatment an effective amount of a compound, or a pharmaceutically acceptable salt or prodrug of the compound of Formulae I-II, which functions as a caspase cascade activator and inducer of apoptosis.

The present invention also includes a therapeutic method comprising administering to an animal an effective amount of a compound, or a pharmaceutically acceptable salt or prodrug of said compound of Formulae I-II, wherein said therapeutic method is useful to treat cancer, which is a group of diseases characterized by the uncontrolled growth and spread of abnormal cells. Such diseases include, but are not limited to, Hodgkin's disease, non-Hodgkin's lymphomas, acute lymphocytic leukemia, chronic lymphocytic leukemia, acute and chronic myelogenous lymphomas, multiple myeloma, neuroblastoma, breast carcinomas, ovarian carcinomas, lung carcinomas, Wilms' tumor, cervical carcinomas, testicular carcinomas, soft-tissue sarcomas, primary macroglobulinemia, bladder carcinomas, chronic granulocytic leukemia, primary brain carcinomas, malignant melanoma, small-cell lung carcinomas, stomach carcinomas, colon carcinomas, malignant pancreatic insulinoma, malignant carcinoid carcinomas, malignant melanomas, choriocarcinomas, mycosis fungoides, head or neck carcinomas, osteogenic sarcoma, pancreatic carcinomas, acute granulocytic leukemia, hairy cell leukemia, neuroblastoma, rhabdomyosarcoma, Kaposi's sarcoma, genitourinary carcinomas, thyroid carcinomas, esophageal carcinomas, malignant hypercalcemia, cervical hyperplasia, renal cell carcinomas, endometrial carcinomas, polycythemia vera, essential thrombocytosis, adrenal cortex carcinomas, skin cancer, and prostatic carcinomas (e.g. hormone dependent and hormone independent).

In practicing the therapeutic methods, effective amounts of compositions containing therapeutically effective concentrations of the compounds formulated for oral, intravenous, local and topical application, for the treatment of neoplastic diseases and other diseases in which caspase cascade mediated physiological responses are implicated, are administered to an individual exhibiting the symptoms of one or more of these disorders. The amounts are effective to ameliorate or eliminate one or more symptoms of the disorders. An effective amount of a compound for treating a particular disease is an amount that is sufficient to ameliorate, or in some manner reduce, the symptoms associated with the disease. Such amount may be administered as a single dosage or may be administered according to a regimen, whereby it is effective. The amount may cure the disease but, typically, is administered in order to ameliorate the symptoms of the disease. Typically, repeated administration is required to achieve the desired amelioration of symptoms In another embodiment, a pharmaceutical composition comprising a compound, or a pharmaceutically acceptable salt of said compound of Formulae I-II, which functions as a caspase cascade activator and inducer of apoptosis in combination with a pharmaceutically acceptable vehicle is provided.

Another embodiment of the present invention is directed to a composition effective to inhibit neoplasia comprising a compound, or a pharmaceutically acceptable salt or prodrug of said compound of Formulae I-II, which functions as a caspase cascade activator and inducer of apoptosis, in combination with at least one known cancer chemotherapeutic agent, or a pharmaceutically acceptable salt of said agent. Examples of known cancer chemotherapeutic agents which may be used for combination therapy include, but not are limited to alkylating agents such as busulfan, cis-platin, mitomycin C, and carboplatin; antimitotic agents such as colchicine, vinblastine, paclitaxel, and docetaxel; topo I inhibitors such as camptothecin and topotecan; topo II inhibitors such as doxorubicin and etoposide; RNA/DNA antimetabolites such as 5-azacytidine, 5-fluorouracil and methotrexate; DNA antimetabolites such as 5-fluoro-2'-deoxy-uridine, ara-C, hydroxyurea and thioguanine; antibodies such as Herceptin® or Rituxan®. Other known cancer chemotherapeutic agents which may be used for combination therapy mitoguazone, epirubicin, aclarubicin, bleomycin, mitoxantrone, elliptinium, fludarabine, octreotide, retinoic acid, tamoxifen and alanosine.

In practicing the methods of the present invention, the compound of the invention may be administered together with at least one known chemotherapeutic agent as part of a unitary pharmaceutical composition. Alternatively, the compound of the invention may be administered apart from at least one known cancer chemotherapeutic agent. In one embodiment, the compound of the invention and at least one known cancer chemotherapeutic agent are administered substantially simultaneously, i.e. the compounds are administered at the same time or one after the other, so long as the compounds reach therapeutic levels in the blood at the same time. On another embodiment, the compound of the invention and at least one known cancer chemotherapeutic agent are administered according to their individual dose schedule, so long as the compounds reach therapeutic levels in the blood.

Another embodiment of the present invention is directed to a composition effective to inhibit neoplasia comprising a bioconjugates of said compound of Formulae I-II, which functions as a caspase cascade activator and inducer of apoptosis, in bioconjugation with at least one known therapeutically useful antibody, such as Herceptin® or Rituxan®, growth factors such as DGF, NGF, cytokines such as IL-2, IL-4, or any molecule that binds to the cell surface. The antibodies and other molecules will deliver the compound of Formulae I-II to its targets and make it an effective anticancer agent. The bioconjugates could also enhance the anticancer effect of therapeutically useful antibodies, such as Herceptin® or Rituxan®.

Similarly, another embodiment of the present invention is directed to a composition effective in inhibiting neoplasia comprising a compound, or a pharmaceutically acceptable salt or prodrug of said compound of Formulae I-II, which functions as a caspase cascade activator and inducer of apoptosis, in combination with radiation therapy. In this embodiment, the compound of the invention may be administered at the same time as the radiation therapy is administered or at a different time.

Yet another embodiment of the present invention is directed to a composition effective for post-surgical treatment of cancer, comprising a compound, or a pharmaceutically acceptable salt or prodrug of said compound of Formulae I-II, which functions as a caspase cascade activator and inducer of apoptosis. The invention also relates to a method of treating cancer by surgically removing the cancer and then treating the animal with one of the pharmaceutical compositions described herein.

A wide range of immune mechanisms operate rapidly following exposure to an infectious agent. Depending on the type of infection, rapid clonal expansion of the T and B lymphocytes occurs to combat the infection. The elimination of the effector cells following an infection is one of the major mechanisms for maintaining immune homeostasis. The elimination of the effector cells has been shown to be regulated by apoptosis. Autoimmune diseases have lately been determined to occur as a consequence of deregulated cell death. In certain autoimmune diseases, the immune system directs its powerful cytotoxic effector mechanisms against specialized cells such as oligodendrocytes in multiple sclerosis, the beta cells of the pancreas in diabetes mellitus, and thyrocytes in Hashimoto's thyroiditis (Ohsako, S. & Elkon, K. B., *Cell Death Differ.* 6:13-21 (1999)). Mutations of the gene encoding the lymphocyte apoptosis receptor Fas/APO-1/CD95 are reported to be associated with defective lymphocyte apoptosis and autoimmune lymphoproliferative syndrome (ALPS), which is characterized by chronic, histologically benign splenomegaly, generalized lymphadenopathy, hypergammaglobulinemia, and autoantibody formation. (Infante, A. J., et al., *J. Pediatr.* 133:629-633 (1998) and Vaishnaw, A. K., et al., *J. Clin. Invest.* 103:355-363 (1999)). It was reported that overexpression of Bcl-2, which is a member of the bcl-2 gene family of programmed cell death regulators with anti-apoptotic activity, in developing B cells of transgenic mice, in the presence of T cell dependent costimulatory signals, results in the generation of a modified B cell repertoire and in the production of pathogenic autoantibodies (Lopez-Hoyos, M., et al., *Int. J. Mol. Med.* 1:475-483 (1998)). It is therefore evident that many types of autoimmune disease are caused by defects of the apoptotic process. One treatment strategy for such diseases is to turn on apoptosis in the lymphocytes that are causing the autoimmune disease (O'Reilly, L. A. & Strasser, A., *Inflamm. Res.* 48:5-21 (1999)).

Fas-Fas ligand (FasL) interaction is known to be required for the maintenance of immune homeostasis. Experimental autoimmune thyroiditis (EAT), characterized by autoreactive T and B cell responses and a marked lymphocytic infiltration of the thyroid, is a good model to study the therapeutic effects of FasL. Batteux, F., et al., (*J. Immunol.* 162:603-608 (1999)) reported that by direct injection of DNA expression vectors encoding FasL into the inflamed thyroid, the development of lymphocytic infiltration of the thyroid was inhibited and induction of infiltrating T cells death was observed. These results show that FasL expression on thyrocytes may have a curative effect on ongoing EAT by inducing death of pathogenic autoreactive infiltrating T lymphocytes.

Bisindolylmaleimide VIII is known to potentiate Fas-mediated apoptosis in human astrocytoma 1321N1 cells and in Molt-4T cells; both of which were resistant to apoptosis induced by anti-Fas antibody in the absence of bisindolylmaleimide VIII. Potentiation of Fas-mediated apoptosis by bisindolyltmaleimide VIII was reported to be selective for activated, rather than non-activated, T cells, and was Fas-dependent. Zhou T., et al., (*Nat. Med.* 5:42-48 (1999)) reported that administration of bisindolylmaleimide VIII to rats during autoantigen stimulation prevented the development of symptoms of T cell-mediated autoimmune diseases in two models, the Lewis rat model of experimental allergic encephalitis and the Lewis adjuvant arthritis model. Therefore, the application of a Fas-dependent apoptosis enhancer such as bisindolylmaleimide VIII may be therapeutically useful for the more effective elimination of detrimental cells and inhibition of T cell-mediated autoimmune diseases. Therefore an effective amount of a compound, or a pharmaceutically acceptable salt or prodrug of the compound of Formulae I-II, which functions as a caspase cascade activator and inducer of apoptosis, should be an effective treatment for autoimmune diseases.

Psoriasis is a chronic skin disease that is characterized by scaly red patches. Psoralen plus ultraviolet A (PUVA) is a widely used and effective treatment for psoriasis vulgaris and Coven, et al., *Photodermatol. Photoimmunol. Photomed.* 15:22-27 (1999), reported that lymphocytes treated with psoralen 8-MOP or TMP and UVA, displayed DNA degradation patterns typical of apoptotic cell death. Ozawa, et al., *J. Exp. Med.* 189:711-718 (1999) reported that induction of T cell apoptosis could be the main mechanism by which 312-nm UVB resolves psoriasis skin lesions. Low doses of methotrexate may be used to treat psoriasis to restore a clinically normal skin. Heenen, et al., *Arch. Dermatol. Res.* 290:240-245 (1998), reported that low doses of methotrexate may induce apoptosis and that this mode of action could explain the reduction in epidermal hyperplasia during treatment of psoriasis with methotrexate. Therefore, an effective amount of a compound, or a pharmaceutically acceptable salt or prodrug of the compound of Formulae I-II, which functions as a caspase cascade activator and inducer of apoptosis, should be an effective treatment for psoriasis.

Synovial cell hyperplasia is a characteristic of patients with rheumatoid arthritis (RA). It is believed that excessive proliferation of RA synovial cells, as well as defects in synovial cell death, may be responsible for synovial cell hyperplasia. Wakisaka, et al., *Clin. Exp. Immunol.* 114:119-128 (1998), found that although RA synovial cells could die via apoptosis through a Fas/FasL pathway, apoptosis of synovial cells was inhibited by proinflammatory cytokines present within the synovium. Wakisaka, et al. also suggested that inhibition of apoptosis by the proinflammatory cytokines may contribute to the outgrowth of synovial cells, and lead to pannus formation and the destruction of joints in patients with RA. Therefore, an effective amount of a compound, or a pharmaceutically acceptable salt or prodrug of the compound of Formulae I-II, which functions as a caspase cascade activator and inducer of apoptosis, should be an effective treatment for rheumatoid arthritis.

There has been an accumulation of convincing evidence that apoptosis plays a major role in promoting resolution of the acute inflammatory response. Neutrophils are constitutively programmed to undergo apoptosis, thus limiting their pro-inflammatory potential and leading to rapid, specific, and non-phlogistic recognition by macrophages and semi-professional phagocytes (Savill, J., *J. Leukoc. Biol.* 61:375-380 (1997)). Boirivant, et al., *Gastroenterology* 116:557-565 (1999), reported that lamina propria T cells, isolated from areas of inflammation in Crohn's disease, ulcerative colitis, and other inflammatory states, manifest decreased CD2 pathway-induced apoptosis. In addition, studies of cells from inflamed Crohn's disease tissue indicate that this defect is accompanied by elevated Bcl-2 levels. Therefore, an effective amount of a compound, or a pharmaceutically acceptable salt or prodrug of the compound of Formulae I-II, which functions as a caspase cascade activator and inducer of apoptosis, should be an effective treatment for inflammation.

Pharmaceutical compositions within the scope of this invention include all compositions wherein the compounds of the present invention are contained in an amount that is effective to achieve its intended purpose. While individual needs vary, determination of optimal ranges of effective amounts of each component is within the skill of the art. Typically, the compounds may be administered to animals, e.g., mammals, orally at a dose of 0.0025 to 50 mg/kg of body weight, per day, or an equivalent amount of the pharmaceutically acceptable salt thereof, to a mammal being treated for apoptosis-mediated disorders. Preferably, about 0.01 to about 10 mg/kg of body weight is orally administered to treat or prevent such disorders. For intramuscular injection, the dose is generally about one-half of the oral dose. For example, a suitable intramuscular dose would be about 0.0025 to about 25 mg/kg of body weight, and most preferably, from about 0.01 to about 5 mg/kg of body weight. If a known cancer chemotherapeutic agent is also administered, it is administered in an amount that is effective to achieve its intended purpose. The amounts of such known cancer chemotherapeutic agents effective for cancer are well known to those of skill in the art.

The unit oral dose may comprise from about 0.01 to about 50 mg, preferably about 0.1 to about 10 mg of the compound of the invention. The unit dose may be administered one or more times daily as one or more tablets each containing from about 0.1 to about 10, conveniently about 0.25 to 50 mg of the compound or its solvates.

In a topical formulation, the compound may be present at a concentration of about 0.01 to 100 mg per gram of carrier.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which may be used pharmaceutically. Preferably, the preparations, particularly those preparations which may be administered orally and which may be used for the preferred type of administration, such as tablets, dragees, and capsules, and also preparations which may be administered rectally, such as suppositories, as well as suitable solutions for administration by injection or orally, contain from about 0.01 to 99 percent, preferably from about 0.25 to 75 percent of active compound(s), together with the excipient.

Also included within the scope of the present invention are the non-toxic pharmaceutically acceptable salts of the compounds of the present invention. Acid addition salts are formed by mixing a solution of the particular apoptosis inducers of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, and the like. Basic salts are formed by mixing a solution of the particular apoptosis inducers of the present invention with a solution of a pharmaceutically acceptable non-toxic base such as sodium hydroxide, potassium hydroxide, choline hydroxide, sodium carbonate, Tris, N-methyl-glucamine and the like.

The pharmaceutical compositions of the invention may be administered to any animal which may experience the beneficial effects of the compounds of the invention. Foremost among such animals are mammals, e.g., humans and veterinary animals, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use may be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye stuffs or pigments may be added to the tablets or dragee coatings, for example, for identification or in order to characterize combinations of active compound doses.

Other pharmaceutical preparations which may be used orally include push-fit capsules made of gelatin, as well as soft, sealed capsules made of gelatin and a plasticizer such as glycerol or sorbitol. The push-fit capsules may contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which may be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400), or cremophor, or cyclodextrins. Aqueous injection suspensions may contain substances which increase the viscosity of the suspension include, for example, sodium carboxymethyl cellulose, sorbitol, and/or dextran. Optionally, the suspension may also contain stabilizers.

In accordance with one aspect of the present invention, compounds of the invention are employed in topical and parenteral formulations and are used for the treatment of skin cancer.

The topical compositions of this invention are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included as well as agents imparting color or fragrance, if desired. Additionally, transdermal penetration enhancers may be employed in these topical formulations. Examples of such enhancers are found in U.S. Pat. Nos. 3,989,816 and 4,444,762.

Creams are preferably formulated from a mixture of mineral oil, self-emulsifying beeswax and water in which mixture the active ingredient, dissolved in a small amount of an oil such as almond oil, is admixed. A typical example of such a cream is one which includes about 40 parts water, about 20 parts beeswax, about 40 parts mineral oil and about 1 part almond oil.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLE 1

1-[2,5-Bis(2,2,2-trifluoroethoxy)phenyl]-3-(4-methylphenyl)-2-propen-1-one

The title compound was prepared by heating a mixture of 2,5-bis(2,2,2-trifluoroethoxy)acetophenone (200 mg, 0.633 mmol), p-tolualdehyde (75 ul, 0.633 mmol), methanol (5 ml) and NaOH (200 ul, 10M) for 24 h. The mixture was cooled to room temperature, diluted with ethyl acetate (100 ml), wash with water and saturated aqueous NaCl, dried over anhydrous sodium sulfate and then concentrated in vacuo. The residue was purified by column chromatography using hexane:ethyl acetate (4:1) to give a yellow solid (32 mg, 12.2%). $^1$H NMR (CDCl$_3$): 7.67 (d, J=15.6 Hz, 1H), 7.50 (d, J=8.4 Hz, 2H), 7.40 (d, J=15.6 Hz, 1H), 7.28 (d, J=3.3 Hz, 1H), 7.22 (d, J=8.1 Hz, 2H), 7.12 (dd, J=3.3, 9.3 Hz, 1H), 6.96 (d, J=8.7 Hz, 1H), 4.44-4.33 (m, 4H), 2.39 (s, 3H).

EXAMPLE 2

1-[2,5-Bis(2,2,2-trifluoroethoxy)phenyl]-3-(4-methoxyphenyl)-2-propen-1-one

The title compound was prepared by heating a mixture of 2,5-bis(2,2,2-trifluoroethoxy)acetophenone (200 mg, 0.633 mmol) and p-anisaldehyde (77 ul, 0.633 mmol) similar to Example 1 and isolated as a yellow solid (75 mg, 27.3%). $^1$H NMR (CDCl$_3$): 7.66 (d, J=15.9 Hz, 1H), 7.56 (d, J=9.0 Hz, 2H), 7.32 (d, J=15.6 Hz, 1H), 7.28 (d, J=3.3 Hz, 2H), 7.11 (dd, J=3.3, 9.0 Hz, 1H), 6.94 (t, J=8.7 Hz, 2H), 4.44-4.33 (m, 4H), 3.86 (s, 3H).

EXAMPLE 3

1-[2,5-Bis(2,2,2-trifluoroethoxy)phenyl]-3-phenyl-2-propen-1-one

The title compound was prepared by heating a mixture of 2,5-bis(2,2,2-trifluoroethoxy)acetophenone (200 mg, 0.633 mmol) and benzaldehyde (64 ul, 0.633 mmol) similar to Example 1 and isolated as a yellow solid (7.2 mg, 2.8%). $^1$H NMR (CDCl$_3$): 7.70 (d, J=16.2 Hz, 1H), 7.62-7.59 (m, 2H), 7.45 (d, J=15.9 Hz, 1H), 7.41 (t, J=3.2 Hz, 3H), 7.29 (d, J=3.3 Hz, 1H), 7.13 (dd, J=3.3, 9.3 Hz, 1H), 6.96 (d, J=9.0 Hz, 1H), 4.45-4.34 (m, 4H).

EXAMPLE 4

1-[2,5-Bis(2,2,2-trifluoroethoxy)phenyl]-3-[4-(trifluoromethyl)phenyl]-2-propen-1-one The title compound was prepared by heating a mixture of 2,5-bis(2,2,2-trifluoroethoxy)acetophenone (200 mg, 0.633 mmol) and α,α,α-trifluoro-p-tolualdehyde (86 ul, 0.633 mmol) similar to Example 1 and isolated as a yellow solid (60.1 mg, 12.7%). $^1$H NMR (CDCl$_3$): 7.70 (d, J=15.6 Hz, 1H), 7.67 (q, J=8.6, 14.9 Hz, 4H), 7.55 (d, J=15.6 Hz, 1H), 7.33 (d, J=3.3 Hz, 1H), 7.15 (dd, J=3.3, 9.0 Hz, 1H), 6.95 (d, J=9.0 Hz, 1H), 4.46-4.34 (m, 4H).

EXAMPLE 5

1-[2,5-Bis(2,2,2-trifluoroethoxy)phenyl]-3-(2-methoxyphenyl)-2-propen-1-one

The title compound was prepared by heating a mixture of 2,5-bis(2,2,2-trifluoroethoxy)acetophenone (200 mg, 0.633 mmol) and o-anisaldehyde (77 ul, 0.633 mmol) similar to Example 1 and isolated as a yellow solid (107 mg, 39%). $^1$H NMR (CDCl$_3$): 8.03 (d, J=15.9 Hz, 1H), 7.61 (dd, J=1.4, 7.7 Hz, 1H), 7.44 (d, J=16.2 Hz, 1H), 7.40-7.34 (m, 1H), 7.25 (d, J=3.3 Hz, 1H), 7.09 (dd, J=3.0, 8.7 Hz, 1H), 7.00-6.94 (m, 2H), 6.92 (d, J=9.3 Hz, 1H), 4.42-4.32 (m, 4H), 3.86 (s, 3H).

EXAMPLE 6

1-[2,5-Bis(2,2,2-trifluoroethoxy)phenyl]-3-(4-chlorophenyl)-2-propen-1-one

The title compound was prepared by stirring a mixture of 2,5-bis(2,2,2-trifluoroethoxy)acetophenone (200 mg, 0.633 mmol), 4-chlorobenzaldehyde (89 mg, 0.633 mmol), methanol (5 ml) and saturated NaOH (200 ul) at room temperature for 4 h. The mixture was diluted with ethyl acetate (100 ml), wash with water (50 ml) and saturated aqueous NaCl (50 ml), dried over anhydrous sodium sulfate and concentrated in vacuo. The residue was purified by column chromatography using hexane:ethyl acetate (5:1, 4:1) to give a yellow solid (143 mg, 51%). $^1$H NMR (CDCl$_3$): 7.65 (d, J=15.9 Hz, 1H), 7.54 (d, J=8.4 Hz, 2H), 7.44 (d, J=15.9 Hz, 1H), 7.38 (d, J=8.4 Hz, 2H), 7.31 (d, J=3.3 Hz, 1H), 7.14 (dd, J=3.3, 9.3 Hz, 1H), 6.95 (d, J=9.0 Hz, 1H), 4.45-4.32 (m, 4H).

EXAMPLE 7

1-[2,5-Bis(2,2,2-trifluoroethoxy)phenyl]-3-[3-(trifluoromethyl)phenyl]-2-propen-1-one The title compound was prepared from a mixture of 2,5-bis(2,2,2-trifluoroethoxy)acetophenone (200 mg, 0.633 mmol) and 3-(trifluoromethyl)benzaldehyde (85 ul, 0.633 mmol) similar to Example 6 and isolated as a yellow solid (88 mg, 30%). $^1$H NMR (CDCl3): 7.86 (s, 1H), 7.76-7.50 (m, 5H), 7.35 (d, J=3.0 Hz, 1H), 7.14 (dd, J=3.3, 9.3 Hz, 1H), 6.94 (d, J=9.0 Hz, 1H), 4.47-4.32 (m, 4H).

EXAMPLE 8

1-[2,5-Bis(2,2,2-trifluoroethoxy)phenyl]-3-[2-(trifluoromethyl)phenyl]-2-propen-1-one The title compound was prepared from a mixture of 2,5-bis(2,2,2-trifluoroethoxy)acetophenone (200 mg, 0.633 mmol) and 2-(trifluoromethyl)benzaldehyde (83 ul, 0.633 mmol) similar to Example 6 and isolated as a pale white-yellow solid (26 mg, 9%). $^1$H NMR (CDCl$_3$): 8.02 (d, J=16.5 Hz, 1H), 7.82 (d, J=7.5 Hz, 1H), 7.72 (d, J=7.5 Hz, 1H), 7.62-7.47 (m, 2H), 7.39 (d, J=15.6 Hz, 1H), 7.29 (d, J=3.3 Hz, 1H), 7.14 (dd, J=3.2, 8.9 Hz, 1H), 6.95 (d, J=9.0 Hz, 1H).

EXAMPLE 9

1-[2,5-Bis(2,2,2-trifluoroethoxy)phenyl]-3-(3,4,5-trimethoxyphenyl)-2-propen-1-one The title compound was prepared from a mixture of 2,5-bis(2,2,2-trifluoroethoxy)acetophenone (200 mg, 0.633 mmol) and 3,4,5-trimethoxybenzaldehyde (124 mg, 0.633 mmol) similar to Example 6 and isolated as a bright yellow solid (120 mg, 38%), $^1$H NMR (CDCl$_3$): 7.65 (d, J=15.6 Hz, 1H), 7.42 (d, J=15.6 Hz, 1H), 7.34 (d, J=3.3 Hz, 1H), 7.12 (dd, J=3.3, 9.0 Hz, 1H), 6.93 (d, J=9.0 Hz, 1H), 6.85 (s, 2H), 4.48-4.34 (m, 4H), 3.90 (d, J=1.8 Hz, 9H).

EXAMPLE 10

1-[2,5-Bis(2,2,2-trifluoromethoxy)phenyl]-3-(3,4-dimethoxyphenyl)-2-propen-1-one The title compound was prepared from a mixture of 2,5-bis(2,2,2-trifluoroethoxy)acetophenone (200 mg, 0.633 mmol) and 3,4-dimethoxybenzaldehyde (105 mg, 0.633 mmol) similar to Example 6 and isolated as a bright yellow solid (74 mg, 25%). $^1$H NMR (CDCl$_3$): 7.69 (d, J=15.6 Hz, 1H), 7.37 (d, J=15.6 Hz, 1H), 7.33 (d, J=3.0 Hz, 1H), 7.20 (d, J=2.7 Hz, 1H), 7.17 (s, 1H), 7.13 (dd, J=3.2, 8.9 Hz, 1H), 6.95 (d, J=8.7 Hz, 1H), 6.90 (d, J=8.7 Hz, 1H), 4.46-4.35 (m, 4H), 3.94 (d, J=2.4 Hz, 6H).

EXAMPLE 11

1-[2,5-Bis(2,2,2-trifluoroethoxy)phenyl]-3-(3-methoxyphenyl)-2-propen-1-one

The title compound was prepared from a mixture of 2,5-bis(2,2,2-trifluoroethoxy)acetophenone (200 mg, 0.633 mmol) and m-anisaldehyde (77 ul, 0.633 mmol) similar to Example 6 and isolated as a light yellow solid (74 mg, 27%). $^1$H NMR (CDCl$_3$): 7.67 (d, J=15.6 Hz, 1H), 7.44 (d, J=15.6 Hz, 1H), 7.34 (s, 1H), 7.30 (dd, J=2.4, 5.7 Hz, 1H), 7.18 (d, J=7.5 Hz, 1H), 7.11 (dd, J=3.2, 8.9 Hz, 2H), 6.97 (dd, J=0.9, 2.7 Hz, 1H), 6.93 (d, J=9.0 Hz, 1H), 4.44-4.33 (m, 4H), 3.83 (s, 3H).

EXAMPLE 12

1-[2,5-Bis(2,2,2-trifluoroethoxy)phenyl]-3-(3-methylphenyl)-2-propen-1-one

The title compound was prepared from a mixture of 2,5-bis(2,2,2-trifluoroethoxy)acetophenone (200 mg, 0.633 mmol) and m-tolualdehyde (75 ul, 0.633 mmol) similar to Example 6 and isolated as a pale yellow solid (76.2 mg, 29%). $^1$H NMR (CDCl$_3$): 7.66 (d, J=15.9 Hz, 1H), 7.44 (d, J=15.6 Hz, 1H), 7.42-7.38 (m, 2H), 7.31-7.20 (m, 3H), 7.10 (dd, J=3.2, 8.9 Hz, 1H), 6.93 (d, J=9.0 Hz, 1H), 4.43-4.32 (m, 4H), 2.37 (s, 3H).

EXAMPLE 13

1-[2,5-Bis(2,2,2-trifluoroethoxy)phenyl]-3-(2-methyl)phenyl)-2-propen-1-one

The title compound was prepared from a mixture of 2,5-bis(2,2,2-trifluoroethoxy)acetophenone (200 mg, 0.633 mmol) and o-tolualdehyde (75 ul, 0.633 mmol) similar to Example 6 and isolated as a dense tan colored liquid (116 mg, 44%). ¹H NMR (CDCl₃): 8.01 (d, J=15.6 Hz, 1H), 7.66 (d, J=7.8 Hz, 1H), 7.37 (d, J=15.6 Hz, 1H), 7.28 (d, J=3.0 Hz, 1H), 7.24-7.18 (m, 1H), 7.11 (d, J=2.7 Hz, 1H), 7.08 (dd, J=3.0, 5.7 Hz, 1H), 6.92 (d, J=8.7 Hz, 1H), 6.78-6.68 (m, 1H), 4.42-4.30 (m, 4H), 2.43 (s, 3H).

EXAMPLE 14

1-[2,5-Bis(2,2,2-trifluoroethoxy)phenyl]-3-[2-(chloro)phenyl]-2-propen-1-one The title compound was prepared from a mixture of 2,5-bis(2,2,2-trifluoroethoxy)acetophenone (100 mg, 0.317 mmol) and 2-chlorobenzaldehyde (36 ul, 0.317 mmol) similar to Example 6. The residue was purified with hexane: ethylacetate (5:1, 4:1) to yield a light yellow solid (13.5 mg, 9.7%). ¹H NMR (CDCl₃): 8.10 (d, J=15.6 Hz, 1H), 7.73 (dd, J=2.3, 7.1 Hz, 1H), 7.43 (d, J=9.3 Hz, 1H), 7.41 (d, J=15.9 Hz, 1H), 7.33 (t, J=2.1 Hz, 1H), 7.32 (s, 1H), 7.3 (d, J=3.0 Hz, 1H), 7.14 (dd, J=3.2 Hz, 9.2, 1H), 6.96 (d, J=9.0 Hz, 1H), 4.45-4.34 (m, 4H).

EXAMPLE 15

1-[2,5-Bis(2,2,2-trifluoroethoxy)phenyl]-3-(4-nitrophenyl)-2-propen-1-one

The title compound was prepared by stirring a mixture of 2,5-bis(2,2,2-trifluoroethoxy)acetophenone (200 mg, 0.633 mmol), 4-nitrobenzaldehyde (96 mg, 0.633 mmol), ethanol (5 ml) and saturated NaOH (50 ul) at room temperature for 4 h. The mixture was diluted with ethyl acetate (100 ml), washed with water and saturated NaCl. The crude was dried over anhydrous sodium sulfate and then concentrated in vacuo. The residue was purified by column chromatography using hexane:ethyl acetate (4:1, 3:1) to give a yellow solid (33 mg, 12%). ¹H NMR (CDCl₃): 8.26 (d, J=9.0 Hz, 2H), 7.74 (d, J=9.0 Hz, 2H), 7.72 (d, J=16.2 Hz, 1H), 7.61 (d, J=15.6 Hz, 1H), 7.36 (d, J=3.0 Hz, 1H), 7.18 (dd, J=3.0, 9.0 Hz, 1H), 6.96 (d, J=9.0 Hz, 1H), 4.49-4.35 (m, 4H).

EXAMPLE 16

1-[2,5-Bis(2,2,2-trifluoroethoxy)phenyl]-3-(2-pyridyl)-2-propen-1-one

The title compound was prepared from a mixture of 2,5-bis(2,2,2-trifluoroethoxy)acetophenone (100 mg, 0.316 mmol) and 2-pyridine carboxaldehyde (30 ul, 0.316 mmol) similar to Example 15 and isolated as a yellow solid (13 mg, 10%) ¹H NMR (CDCl₃): 8.68-8.65 (m, 1H), 7.79 (d, J=15.6 Hz, 1H), 7.72 (dd, J=1.7, 7.7 Hz, 1H), 7.64 (d, J=15.6 Hz, 1H), 7.53 (d, J=7.8 Hz, 1H), 7.31-7.28 (m, 1H), 7.25 (s, 1H), 7.12 (dd, J=3.2, 8.9 Hz, 1H), 6.96 (d, J=9.3 Hz, 1H), 4.44-4.33 (m, 4H).

EXAMPLE 17

1-[2,5-Bis(2,2,2-trifluoroethoxy)phenyl]-3-(3-pyridyl)-2-propen-1-one

The title compound was prepared from a mixture of 2,5-bis(2,2,2-tifluoroethoxy)acetophenone (100 mg, 0.316 mmol) and 3-pyridine carboxaldehyde (30 ul, 0.316 mmol) similar to Example 15 and isolated as a yellow solid (19 mg, 15%). ¹H NMR (CDCl₃): 8.81 (d, J=2.1 Hz, 1H), 8.62 (dd, J=1.7, 4.7 Hz, 1H), 7.94-7.91 (m, 1H), 7.70 (d, J=15.9 Hz, 1H), 7.55 (d, J=15.9 Hz, 1H), 7.38-7.33 (m, 2H), 7.16 (dd, J=3.2, 8.9 Hz, 1H), 6.95 (d, J=9.0 Hz, 1H), 4.47-4.35 (m, 4H).

EXAMPLE 18

1-[2,5-Bis(2,2,2-trifluoroethoxy)phenyl]-3-(3-nitrophenyl)-2-propen-1-one

The title compound was prepared from a mixture of 2,5-bis(2,2,2-trifluoroethoxy)acetophenone (200 mg, 0.633 mmol), 3-nitrobenzaldehyde (96 mg, 0.633 mmol), methanol (5 ml) and saturated NaOH (50 ul). The mixture was diluted with water (5 ml). The resulting yellow precipitate was collected by filtration, wash with water and dried under vacuum to give yellow solid (129 mg, 45%). ¹H NMR (CDCl₃): 8.48 (s, 1H), 8.28-8.24 (m, 1H), 7.91 (d, J=7.8 Hz, 1H), 7.74 (d, J=15.9 Hz, 1H), 7.61 (d, J=16.2 Hz, 1H), 7.60 (d, J=7.8 Hz, 1H), 7.36 (d, J=3.0 Hz, 1H), 7.18 (dd, J=3.3, 9.0 Hz, 1H), 6.96 (d, J=9.0 Hz, 1H), 4.49-4.36 (m, 4H).

EXAMPLE 19

1-[2,5-Bis(2,2,2-trifluoroethoxy)phenyl]-3-[2,4-bis-(trifluoromethyl)phenyl]prop-2-en-1-one The title compound was prepared from a mixture of 2,5-bis(2,2,2-trifluoroethoxy)acetophenone (200 mg, 0.633 mmol) and 2,4-bis(trifluoromethyl)benzaldehyde (108 ul, 0.633 mmol) similar to Example 6 as a yellow solid (27 mg, 8%). ¹H NMR (CDCl₃): 8.03 (dd, J=2.0, 15.5 Hz, 1H), 7.97 (s, 1H), 7.93 (d, J=8.1 Hz, 1H), 7.86 (d, J=7.2 Hz, 1H), 7.50 (d, J=15.6 Hz, 1H), 7.35 (d, J=3.3 Hz, 1H), 7.18 (dd, J=3.3, 9.0 Hz, 1H), 6.95 (d, J=9.3 Hz, 1H), 4.47-4.35 (m, 4H).

EXAMPLE 20

1-[2,5-Bis(2,2,2-trifluoromethoxy)phenyl]-3-(4-ethoxyphenyl)prop-2-en-1-one

The title compound was prepared from a mixture of 2,5-bis(2,2,2-trifluoroethoxy)acetophenone (100 mg, 0.316 mmol) and 4-ethoxybenzaldehyde (47 mg, 0.316 mmol) similar to Example 18 as a yellow solid (86 mg, 61%). ¹H NMR (CDCl₃): 7.65 (d, J=15.9 Hz, 1H), 7.54 (d, J=8.7 Hz, 2H), 7.30 (d, J=15.6 Hz, 1H), 7.27 (s, 1H), 7.11 (dd, J=3.3, 8.7 Hz, 1H), 6.95 (d, J=9.0 Hz, 1H), 6.91 (d, J=8.7 Hz, 2H), 4.43-4.33 (m, 4H), 4.08 (q, J=7.1 Hz, 2H), 1.44 (s, 3H).

EXAMPLE 21

1-[2,5-Bis(2,2,2-trifluoroethoxy)phenyl]-3-[3-fluoro-4-(trifluoromethyl)phenyl]prop-2-en-1-one The title compound was prepared from a mixture of 2,5-bis(2,2,2-trifluoroethoxy)acetophenone (200 mg, 0.633 mmol) and 3-fluoro-4-(trifluoromethyl)benzaldehyde (91 ul, 0.633 mmol) similar to Example 18 as a yellow solid (164 mg, 53%). ¹H NMR (CDCl₃): 7.65-7.60 (m, 2H), 7.52 (d, J=15.9 Hz, 1H), 7.43-7.37 (m, 2H), 7.32 (d, J=3.3 Hz, 1H), 7.15 (dd, J=3.3, 8.7 Hz, 1H), 6.92 (d, J=9.0 Hz, 1H), 4.45-4.32 (m, 4H).

EXAMPLE 22

1-[2,5-Bis(2,2,2-trifluoroethoxy)phenyl]-3-[2,3-difluoro-4-(trifluoromethyl)phenyl]prop-2-en-1-one The title compound was prepared from a mixture of 2,5-bis(2,2,2-trifluoroethoxy)acetophenone (200 mg, 0.633 mmol) and 2,3-difluoro-4-(trifluoromethyl)benzaldehyde (91 ul, 0.633 mmol) similar to Example 18 as a yellow solid (66 mg, 20%). $^1$H NMR (CDCl$_3$): 7.78 (d, J=15.9 Hz, 1H), 7.64 (d, J=16.2 Hz, 1H), 7.51-7.38 (m, 2H), 7.35 (d, J=3.0 Hz, 1H), 7.18 (dd, J=3.3, 9.0 Hz, 1H), 6.95 (d, J=9.3 Hz, 1H), 4.47-4.35 (m, 4H).

EXAMPLE 23

Identification of 1-[2,5-Bis(2,2,2-trifluoroethoxy) phenyl]-3-[4-(trifluoromethyl)phenyl]-2-propen-1-one and Analogs as Caspase Cascade Activators and Inducers of Apoptosis in Solid Tumor Cells Human breast cancer cell lines T-47D and ZR-75-1 were grown according to media component mixtures designated by American Type Culture Collection+10% FCS (Invitrogen Corporation, Life Technologies Division), in a 5% CO$_2$-95% humidity incubator at 37° C. T-47D and ZR-75-1 cells were maintained at a cell density between 50 and 80% confluency at a cell density of 0.1 to 0.6×10$^6$ cells/ml. Cells were harvested at 600×g and resuspended at 0.65×10$^6$ cells/ml into appropriate media+10% FCS. An aliquot of 45 μl of cells was added to a well of a 96-well microtiter plate containing 2.5 μl of a 10% DMSO in RPMI-1640 media solution containing 0.16 to 100 μM of 1-[2,5-bis(2,2,2-trifluoroethoxy)phenyl]-3-[4-(trifluoromethyl)phenyl]-2-propen-1-one or other test compound (0.016 to 10 μM final). An aliquot of 22.5 μl of cells was added to a well of a 384-well microtiter plate containing 2.5 μl of a 10% DMSO in RPMI-1640 media solution without test compound as the control sample. The samples were mixed by agitation and then incubated at 37° C. for 24 h in a 5% CO$_2$-95% humidity incubator. After incubation, the samples were removed from the incubator and 25 μl of a solution containing 14 μM of N-(Ac-DEVD)-N'-ethoxycarbonyl-R110 (SEQ. ID NO:1) fluorogenic substrate (Cytovia, Inc.; WO99/18856), 20% sucrose (Sigma), 20 mM DTT (Sigma), 200 mM NaCl (Sigma), 40 mM Na PIPES buffer pH 7.2 (Sigma), and 500 μg/ml lysolecithin (Calbiochem) was added. The samples were mixed by agitation and incubated at room temperature. Using a fluorescent plate reader (Model SpectraMax Gemini, Molecular Devices), an initial reading (T=0) was made approximately 1-2 min after addition of the substrate solution, employing excitation at 485 nm and emission at 530 nm, to determine the background fluorescence of the control sample. After the 3 h incubation, the samples were read for fluorescence as above (T=3 h).

Calculation

The Relative Fluorescence Unit values (RFU) were used to calculate the sample readings as follows:

RFU$_{(T=3h)}$−Control RFU$_{(T=0)}$=Net RFU$_{(T=3h)}$

The activity of caspase cascade activation was determined by the ratio of the net RFU value for 1-[2,5-bis(2,2,2-trifluoroethoxy)phenyl]-3-[4-(trifluoromethyl)phenyl]-2-propen-1-one or other test compound to that of control samples. The EC$_{50}$ (nM) was determined by a sigmoidal dose-response response calculation (Prism 2.0, GraphPad Software Inc.). The caspase activity (Ratio) and potency (EC$_{50}$) are summarized in Table I:

TABLE I

| | Caspase Activity and Potency | | | |
|---|---|---|---|---|
| | T-47D | | ZR-75-1 | |
| Example # | Ratio | EC$_{50}$ (nM) | Ratio | EC$_{50}$ (nM) |
| 4 | 25.2 | 5000 | 5.5 | 6000 |
| 3 | 6.8 | 1600 | 3.3 | 5400 |
| 15 | 20.4 | 6800 | 14.9 | 6900 |

Thus, 1-[2,5-bis(2,2,2-trifluoroethoxy)phenyl]-3-[4-(trifluoromethyl)phenyl]-2-propen-1-one (Example 4), 1-[2,5-bis(2,2,2-trifluoroethoxy)phenyl]-3-phenyl-2-propen-1-one (Example 3) and 1-[2,5-bis(2,2,2-trifluoroethoxy)phenyl]-3-(4-nitrophenyl)-2-propen-1-one (Example 15) are identified as potent caspase cascade activators and inducers of apoptosis in solid tumor cells.

EXAMPLE 24

Identification of 1-[2,5-Bis(2,2,2-trifluoroethoxy) phenyl]-3-[4-(trifluoromethyl)phenyl]-2-propen-1-one as Antineoplastic Compound that Inhibits Cell Proliferation (GI$_{50}$)

All the cell lines were grown according to the conditions recommended by American Type Culture Collection. An aliquot of 90 μl of cells (2.2×10$^4$ cells/ml) was added to a well of a 96-well microtiter plate containing 10 μl of a 10% DMSO in RPMI-1640 media solution containing 1 nM to 100 μM of 1-[2,5-bis(2,2,2-trifluoroethoxy)phenyl]-3-[4-(trifluoromethyl)phenyl]-2-propen-1-one (0.1 nM to 10 μM final). An aliquot of 90 μl of cells was added to a well of a 96-well microtiter plate containing 10 μl of a 10% DMSO in RPMI-1640 media solution without compound as the control sample for maximal cell proliferation (A$_{Max}$). The samples were mixed by agitation and then incubated at 37° C. for 48 h in a 5% CO$_2$-95% humidity incubator. After incubation, the samples were removed from the incubator and 20 μl of CellTiter 96 AQ$_{UEOUS}$ One Solution Cell Proliferation™ reagent (Promega) was added. The samples were mixed by agitation and incubated at 37° C. for 2-4 h in a 5% CO$_2$-95% humidity incubator. Using an absorbance plate reader (Model 1420 Wallac Instruments), an initial reading (T=0) was made approximately 1-2 min after addition of the solution, employing absorbance at 490 nm. This determines the possible background absorbance of the test compounds. No absorbance for 1-[2,5-bis(2,2,2-trifluoroethoxy)phenyl]-3-[4-(trifluoromethyl)phenyl]-2-propen-1-one was found at 490 nm. After the 2-4 h incubation, the samples were read for absorbance as above (A$_{Test}$).

Baseline for GI$_{50}$ (dose for 50% inhibition of cell proliferation) of initial cell numbers were determined by adding an aliquot of 90 μl of cells or 90 μl of media, respectively, to wells of a 96-well microtiter plate containing 10 μl of a 10% DMSO in RPMI-1640 media solution. The samples were mixed by agitation and then incubated at 37° C. for 0.5 h in a 5% CO$_2$-95% humidity incubator. After incubation, the samples were removed from the incubator and 20 µl of CellTiter 96 AQ$_{UEOUS}$ One Solution Cell Proliferation™ reagent (Promega) was added. The samples were mixed by agitation and incubated at 37° C. for 2-4 h in a 5% CO$_2$-95% humidity incubator. Absorbance was read as above, ($A_{Start}$) defining absorbance for initial cell number used as baseline in GI$_{50}$ determinations.

Calculation

GI$_{50}$ (dose for 50% inhibition of cell proliferation) is the concentration where $[(A_{Test}-A_{Start})/(A_{Max}-A_{Start})]=0.5$.

The GI50 (nM) are summarized in Table II.

TABLE II

GI$_{50}$ in Cancer Cells

| Cell lines | Example 4 GI50 (nM) |
|---|---|
| T-47D | 1500 |
| SK-Br-3 | 1800 |
| MDA-MB-435 | 3200 |
| MCF-7 | 2400 |
| PC-3 | 3000 |
| HeLa | 2300 |
| DLD-1 | 2500 |
| K562 | 2200 |
| PANC-1 | 3100 |

Thus, 1-[2,5-bis(2,2,2-trifluoroethoxy)phenyl]-3-[4-(trifluoromethyl)-phenyl]-2-propen-1-one (Example 4) is identified as antineoplastic compound that inhibits cell proliferation in a variety of cancer cell lines.

EXAMPLE 25

Figure 1A:
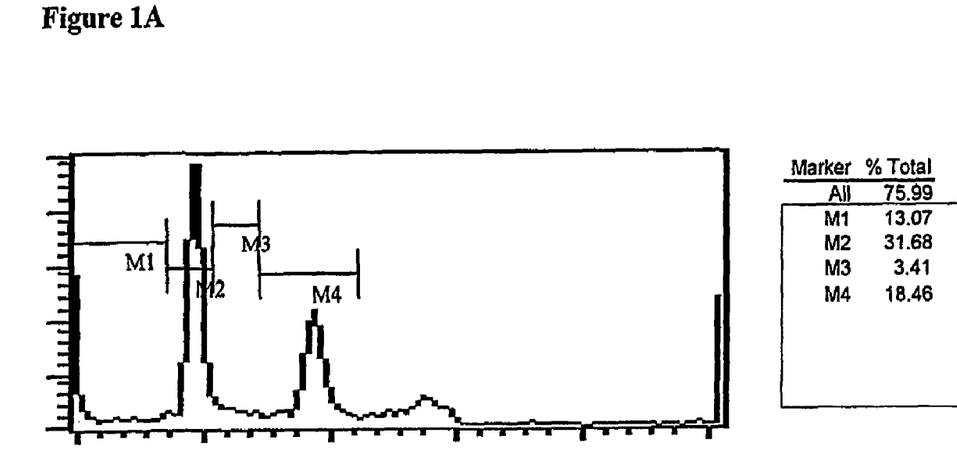
Figure 1B:
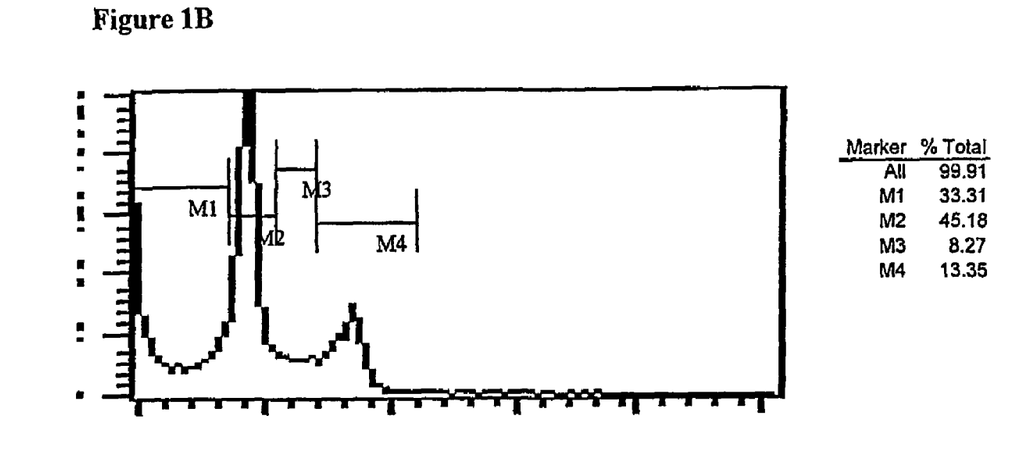

Treatment with 1-[2,5-Bis(2,2,2-trifluoroethoxy) phenyl]-3-[4-(trifluoromethyl)phenyl]-2-propen-1-one Leads to Cell Cycle Arrest and Apoptosis in T-47D Cells T-47D, a breast cancer cell line, was maintained and harvested as described in Example 23. 5×10$^5$ Cells were treated with 10 µM of 1-[2,5-bis(2,2,2-trifluoroethoxy)phenyl]-3-[4-(trifluoromethyl)phenyl]-2-propen-1-one for 48 h at 37° C. As a control, cells were also incubated with equivalent amount of solvent (DMSO). Cells were harvested at 1,200 rpm and then transferred to 12×75 mm polystyrene tubes. Cells were then resuspended in 500 µl of 1% Na Citrate, 0.1% Triton X-100, and 50 µg/ml of propidium iodide and incubated at room temperature for 30 min followed by flow cytometer analysis. All flow cytometry analyses were performed on FACScalibur (Becton Dickinson) using Cell Quest analysis software. The x-axis plotted the amount of fluorescence and the y-axis is plotted the number of cells with the indicated fluorescence. The T-47D control cell population profile is seen in FIG. 1A and the increase in G2/M DNA content cells when treated with 10 µM of 1-[2,5-bis(2,2,2-trifluoroethoxy)phenyl]-3-[4-(trifluoromethyl)phenyl]-2-propen-1-one is seen in FIG. 1B. An increase from 13% to 33% in the sub-diploid DNA content of cells (FIG. 1) is also seen with compound treatment. The sub-diploid amount of DNA is indicative of apoptotic cells which have undergone DNA degradation or fragmentation.

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What is claimed is:

1. A compound of Formula I:

(I)

or pharmaceutically acceptable salts or prodrugs thereof, wherein:

Ar is optionally substituted aryl or optionally substituted heteroaryl;

$R_6$-$R_8$ are independently hydrogen, halo, haloalkyl, aryl, fused aryl, carbocyclic, a heterocyclic group, a heteroaryl group, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, amino, cyano, acylamido, hydroxy, thiol, acyloxy, azido, alkoxy, aryloxy, arylalkoxy, haloalkoxy, carboxy, carbonylamido or alkylthiol; and

$R_9$ and $R_{10}$ are independently hydrogen, alkyl or cycloalkyl;

with the proviso that when Ar is 4-trifluoromethylphenyl, then
(a) at least one of $R_6$-$R_8$ are other than hydrogen; or
(b) Ar is further substituted with at least one group other than hydrogen; or
(c) at least one of $R_9$ and $R_{10}$ is other than hydrogen.

2. The compound of claim 1, wherein $R_9$ and $R_{10}$ are hydrogen.

3. The compound of claim 1, wherein Ar is an optionally substituted phenyl, naphthyl, pyridyl, quinolyl, isoquinolyl, thienyl, furyl, or pyrrolyl.

4. A compound of Formula II:

or pharmaceutically acceptable salts or prodrugs thereof, wherein:

$R_1$-$R_8$ are independently hydrogen, halo, haloalkyl, aryl, fused aryl, carbocyclic, a heterocyclic group, a heteroaryl group, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, amino, cyano, acylamido, hydroxy, thiol, acyloxy, azido, alkoxy, aryloxy, arylalkoxy, haloalkoxy, carboxy, carbonylamido or alkyithiol, each of which is optionally substituted;
provided that when $R_3$ is $CF_3$, then at least one of $R_1$-$R_2$ and $R_4$-$R_8$ is other than hydrogen.

5. The compound of claim 1, wherein said compound is selected from the group consisting of:

1-[2,5-bis(2,2,2-trifluoroethoxy)phenyl]-3-(4-methylphenyl)-2-propen-1-one;
1-[2,5-bis(2,2,2-trifluoroethoxy)phenyl]-3-(4-methoxyphenyl)-2-propen-1-one;
1-[2,5-bis(2,2,2-trifluoroethoxy)phenyl]-3-(2-methoxyphenyl)-2-propen-1-one;
1-[2,5-bis(2,2,2-trifluoroethoxy)phenyl]-3-phenyl-2-propen-1-one;
1-[2,5-bis(2,2,2-trifluoroethoxy)phenyl]-3-(4-chlorophenyl)-2-propen-1-one;
1-[2,5-bis(2,2,2-trifluoroethoxy)phenyl]-3-[2-(trifluoromethyl)phenyl]-2-propen-1-one;
1-[2,5-bis(2,2,2-trifluoroethoxy)phenyl]-3-(3,4-dimethoxyphenyl)-2-propen-1-one;
1-[2,5-bis(2,2,2-trifluoroethoxy)phenyl]-3-(3,4,5-trimethoxyphenyl)-2-propen-1-one;
1-[2,5-bis(2,2,2-trifluoroethoxy)phenyl]-3-[3-(trifluoromethyl)phenyl]-2-propen-1-one;
1-[2,5-bis(2,2,2-trifluoroethoxy)phenyl]-3-(3-methoxyphenyl)-2-propen-1-one;
1-[2,5-bis(2,2,2-trifluoroethoxy)phenyl]-3-(3-methylphenyl)-2-propen-1-one;
1-[2,5-bis(2,2,2-trifluoroethoxy)phenyl]-3-(2-chlorophenyl)-2-propen-1-one;
1-[2,5-bis(2,2,2-trifluoroethoxy)phenyl]-3-(2-methylphenyl)-2-propen-1-one;
1-[2,5-bis(2,2,2-trifluoroethoxy)phenyl]-3-(4-nitrophenyl)-2-propen-1-one;
1-[2,5-bis(2,2,2-trifluoroethoxy)phenyl]-3-(2-pyridyl)-2-propen-1-one;
1-[2,5-bis(2,2,2-trifluoroethoxy)phenyl]-3-(3-pyridyl)-2-propen-1-one;
1-[2,5-bis(2,2,2-trifluoroethoxy)phenyl]-3-(3-nitrophenyl)-2-propen-1-one;
1-[2,5-bis(2,2,2-trifluoroethoxy)phenyl]-3-[2,4-di(trifluoromethyl)-phenyl]-2-propen-1-one;
1-[2,5-bis(2,2,2-trifluoroethoxy)phenyl]-3-(4-ethoxyphenyl)-2-propen-1-one;
1-[2,5-bis(2,2,2-trifluoroethoxy)phenyl]-3-(2,3-difluoro-4-trifluoromethylphenyl)-2-propen-1-one; and
1-[2,5-bis(2,2,2-trifluoroethoxy)phenyl]-3-(3-fluoro-4-trifluoromethylphenyl)-2-propen-1-one.

6. A pharmaceutical composition, comprising the compound of claim 1, and a pharmaceutically acceptable carrier.

7. The pharmaceutical composition of claim 6, further comprising at least one known cancer chemotherapeutic agent, or a pharmaceutically acceptable salt of said agent.

8. The pharmaceutical composition of claim 7, wherein said known cancer chemotherapeutic agent is selected from the group consisting of busulfan, cis-platin, mitomycin C, carboplatin, colchicine, vinblastine, paclitaxel, docetaxel, camptothecin, topotecan, doxorubicin, etoposide, 5-azacytidine, 5-fluorouracil, methotrexate, 5-fluoro-2'-deoxy-uridine, ara-C, hydroxyurea, thioguanine, melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen, and alanosine.

* * * * *

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Fluorogenic substrate

<400> SEQUENCE: 1

Asp Glu Val Asp
1
```